United States Patent [19]
Gates

[11] Patent Number: 5,651,763
[45] Date of Patent: *Jul. 29, 1997

[54] ORTHOPEDIC BELT

[75] Inventor: Yoko C. Gates, San Mateo, Calif.

[73] Assignee: Back-A-Line, Inc., Brisbane, Calif.

[*] Notice: The term of this patent shall not extend beyond the expiration date of Pat. No. 5,429,587.

[21] Appl. No.: 439,581

[22] Filed: May 11, 1995

Related U.S. Application Data

[63] Continuation of Ser. No. 200,842, Feb. 22, 1994, Pat. No. 5,429,587.

[51] Int. Cl.$^6$ .................................................. A61F 5/00
[52] U.S. Cl. ........................................ 602/19; 128/876
[58] Field of Search .................................. 128/869, 876; 602/19; 2/309, 311, 321, 337, 338; 273/117, 119, 143

[56] References Cited

U.S. PATENT DOCUMENTS

| | | | |
|---|---|---|---|
| 2,726,714 | 12/1955 | McAndrews | 128/876 |
| 3,052,236 | 9/1962 | Schrieber . | |
| 3,171,409 | 3/1965 | Cetrone . | |
| 3,400,710 | 9/1968 | Goldstein . | |
| 3,434,469 | 3/1969 | Swift . | |
| 3,713,437 | 1/1973 | Wiedmer . | |
| 3,717,143 | 2/1973 | Johnson . | |
| 4,135,503 | 1/1979 | Romano . | |
| 4,159,020 | 6/1979 | von Soiron . | |
| 4,178,923 | 12/1979 | Curlee . | |
| 4,243,028 | 1/1981 | Puyana . | |
| 4,245,628 | 1/1981 | Eichler . | |
| 4,475,543 | 10/1984 | Brooks . | |
| 4,552,135 | 11/1985 | Racz . | |
| 4,597,386 | 7/1986 | Goldstein . | |
| 4,616,639 | 10/1986 | Huber . | |
| 4,627,109 | 12/1986 | Carabelli . | |
| 4,703,750 | 11/1987 | Sebastian . | |
| 4,745,911 | 5/1988 | Bender . | |
| 4,794,916 | 1/1989 | Porterfield . | |
| 4,796,315 | 1/1989 | Crew . | |
| 4,836,194 | 6/1989 | Sebastian . | |
| 4,941,465 | 7/1990 | Borschneck . | |
| 4,991,573 | 2/1991 | Miller | 602/19 |
| 4,997,438 | 3/1991 | Nipper . | |
| 5,040,524 | 8/1991 | Votel | 602/19 |
| 5,046,488 | 9/1991 | Schiek . | |
| 5,093,931 | 3/1992 | LaBerge | 2/2 |
| 5,178,163 | 1/1993 | Yewer . | |
| 5,316,022 | 5/1994 | Schiek | 128/876 |

Primary Examiner—Michael A. Brown
Attorney, Agent, or Firm—Townsend and Townsend and Crew LLP

[57] ABSTRACT

A lumbosacral support system comprising a belt and an orthopedic pad carried by the belt. The pad has a contoured template surface with a transversely extending central trough portion for accommodating the protruding spinal processes of the wearer when the pad is pressed against the lumbar region, and a pair of raised plateau regions flanking the central trough portion for contacting the erector spinae muscles of the wearer to provide support. The template surface of the pad has a vertical surface contour through the central region approximating the average lordotic curve of a wearer. The belt is longitudinally tapered so the pad is arranged at an angle to vertical to optimally engage the lumbar region of the wearer.

11 Claims, 3 Drawing Sheets

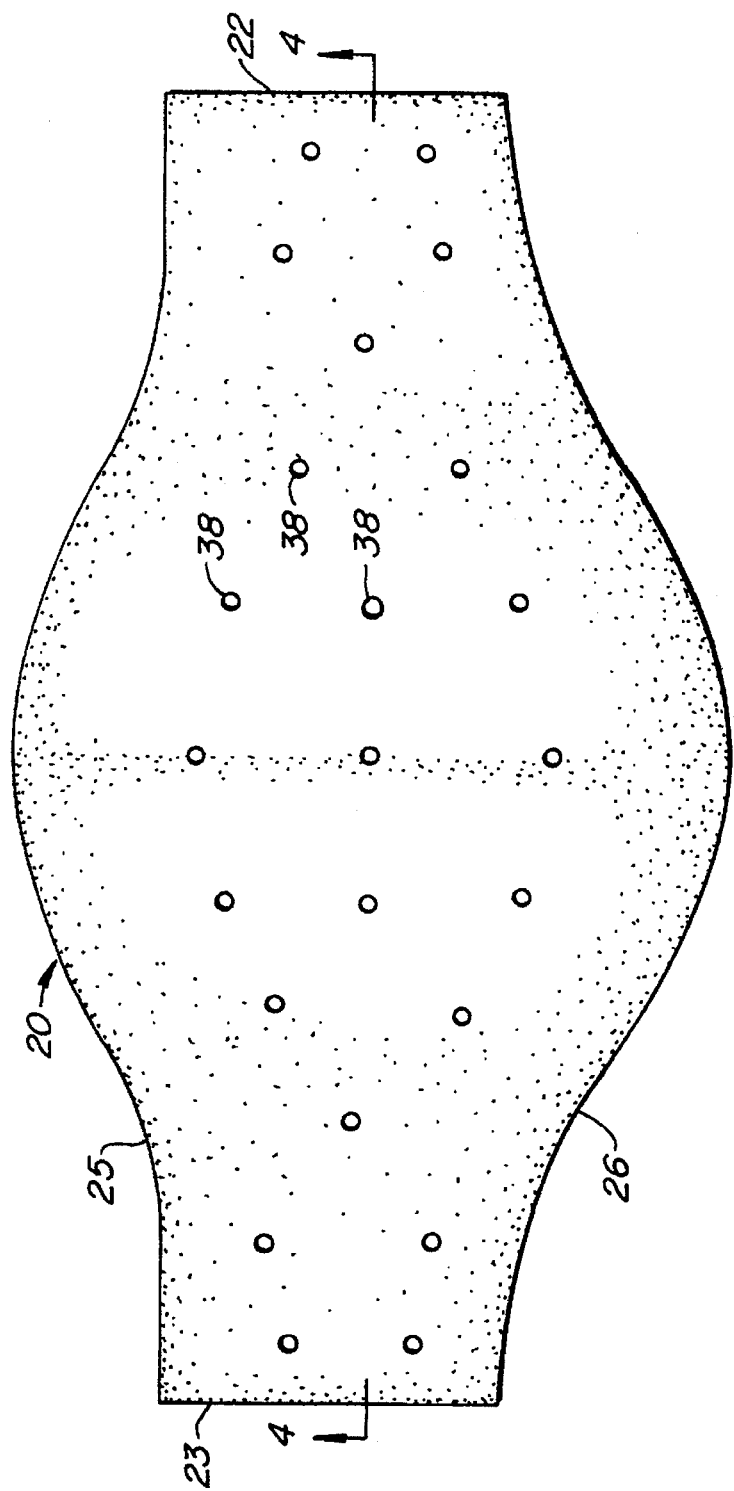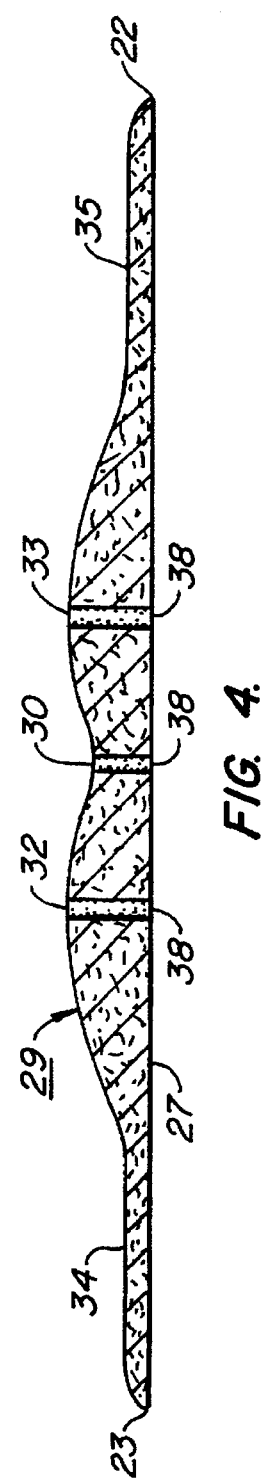

ORTHOPEDIC BELT

This is a Continuation of application Ser. No. 08/200,842 filed Feb. 22, 1994, now U.S. Pat. No. 5,429,587.

BACKGROUND OF THE INVENTION

This invention relates to orthopedic devices of the type used to provide support for the lower back. More particularly, this invention relates to an orthopedic device in the form of a belt adapted to be worn by a user and to provide support for the lower back of the user.

Many orthopedic devices have been proposed, the purpose of which is to provide lower back support to prevent or alleviate lower back pain. Belts designed for this purpose have generally been of two different types. A first type uses some type of conforming pad, typically made of a foam material, with the pad being permanently attached to the belt either inside or outside the fabric comprising the belt, with the pad in a position to be compressed against the lower back region when the belt is arranged about the waist of the user. The second type of device employs an inflatable air bladder having one or more air chambers, the wall of the bladder being sufficiently flexible to enable the air chamber to conform to the shape of the back of the wearer when the belt is attached around the waist. Both types of device suffer from the disadvantage that the portion of the device in contact with the back of the user (i.e., the pad or the air chamber walls) functions to easily conform to the shape of the wearer's back. Consequently, if the lower back is in a position other than the ideal posture, the belt does not promote a change to the proper posture since the contact region of the pad adapts to the shape of the lower back. When this shape is contorted, as for example by performing a stressful lifting routine, the back is not effectively impeded by the device from maneuvering to an improper posture. Efforts to date to design an orthopedic device devoid of these disadvantages have not been successful.

SUMMARY OF THE INVENTION

The invention comprises an orthopedic device which provides yieldable but substantial resistive force to the lower back region of the user so that this region is provided with an idealized contoured template.

A belt is provided with an orthopedic pad at essentially the mid-point of the length of the belt, the pad being preferably confined within a space enclosed by a suitable belt fabric such as nylon or the like. The orthopedic pad has an essentially planar base facing away from the back of the user when the belt is installed and an orthopedic template surface having a compound configuration. The perimeter of the orthopedic pad comprises two essentially straight edge portions at opposing ends thereof, and a pair of curved edges extending therebetween. Each curved edge has a convex shape with the maximum outward excursion at essentially the mid-point of the curve. The template surface of the orthopedic pad has a centrally located hollow region extending transversely of the mid-point thereof, the hollow region being flanked by substantially flat surface regions extending away from the hollow region and gradually descending to flanking valley regions which blend smoothly into the lateral edges of the pad. A portion of the template surface approximates the average lordotic curve of a wearer. The pad is preferably perforated in several spots in order to provide ventilation through the pad. The pad is fabricated from a relatively stiff but resilient material which provides non-conforming yieldable support for the lower back region of the wearer.

The belt has a longitudinal dimension along the top edge thereof which is shorter than the longitudinal dimension along the bottom so that the pad is tilted slightly forwardly when arranged about the waist of the user. This optimizes the angular position of the template surface against the lower back region and accounts for the normal waist and hip measurement differential encountered in users, thereby providing substantially equal intra-abdominal pressure to all parts of the abdomen.

In use, the belt is installed around the waist of the user with the orthopedic pad in contact with the lower back region. When arranged properly along the lower back region, the high points on the template surface of the pad contact the erector spinae muscles along substantially parallel paths with respect to the spine to provide a resistive but yieldable support surface. Thus, any tendency of the lower back region to extend out of the idealized configuration represented by the template surface is opposed by the orthopedic pad. In addition, flexion is opposed by the natural tendency of the proprioceptors of the back (which comprise muscles, ligaments and nerves) to adapt to and allow a smooth firm surface. In addition, during muscle relaxation the pad 20 tends to move away from the spine as an integral unit, which allows the muscle and ligament structure to provide its own support. This tends to substantially reduce or eliminate atrophy of the back muscles.

In an alternate embodiment of the invention, the belt is provided with a plurality of secondary belt loops which can be used to support various tool holders of the type used by workmen. Thus, the belt can be adapted for use in a wide variety of occupations while providing the orthopedic benefit.

For a fuller understanding of the nature and advantages of the invention, reference should be had to the ensuing detailed description taken in conjunction with the accompanying drawings.

BRIEF DESCRIPTION OF THE DRAWINGS

FIG. 3 is a plan view of the template surface of the orthopedic pad;

FIG. 4 is a sectional view taken along lines 4—4 of FIG. 3 showing the template surface contour.

DESCRIPTION OF THE PREFERRED EMBODIMENTS

Figure 1:
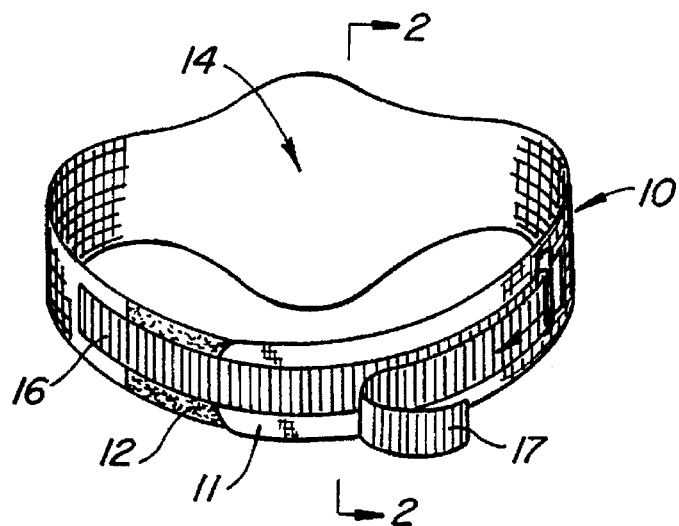
FIG. 1 is a perspective view illustrating a first embodiment of the invention with the belt partially closed.

Turning now to the drawings, FIG. 1 illustrates a first embodiment of the invention. As seen in this Fig., a belt 10 having overlapping ends 11, 12 has a central region generally designated with numeral 14. In region 14, the edges of the belt curve outwardly to a maximum width dimension at essentially the center of region 12. The two overlapping ends 11, 12 are provided with complementary hook and eye fasteners in order to provide an adjustable closure for the belt. A secondary closure is provided by additional belting 16, 17 of reduced width. The belt 10 can be fabricated from any suitable material, such as a Nylon fabric and is preferably a two-ply belt secured around the perimeteral edges so as to enable the retention therewithin of an orthopedic pad illustrated in FIGS. 2-4.

Figure 2:
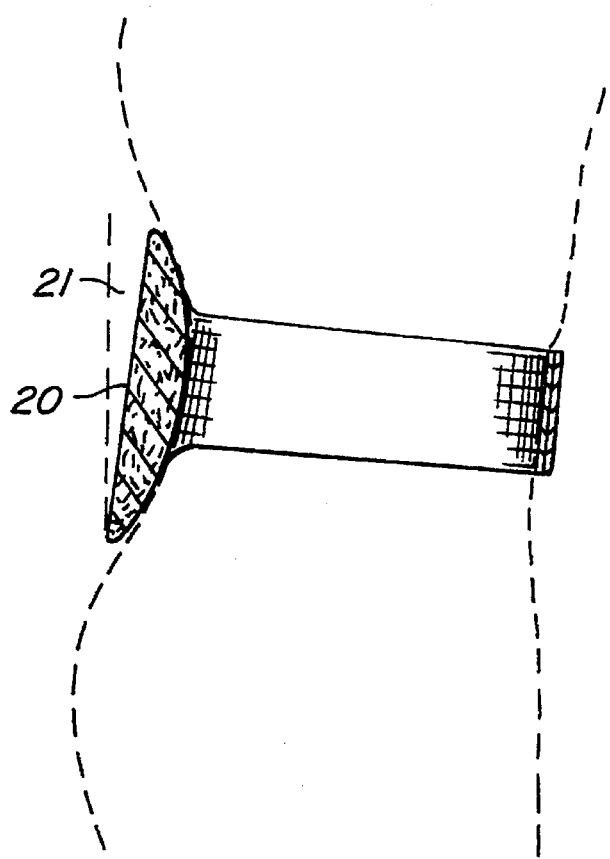
FIG. 2 is a side sectional view taken along lines 2—2 of FIG. 1 and illustrating the pad in place against the lower back region.

FIG. 2 illustrates the embodiment of FIG. 1 secured about the abdomen of a user shown in broken lines with the orthopedic pad 20 in place in the lower back region of the user. The belt 10 is fabricated with a longitudinal taper obtained by providing the belt with a shorter length along the top edge than along the bottom edge. As a consequence, the pad, when installed, resides at an angle 21 with respect to a vertical line drawn perpendicular to the circumference of the user's waist, so that the pad 20 will nest against the lordotic curve of the wearer.

As seen in FIGS. 3 and 4, pad 20 has a pair of opposing straight edge portions 22, 23 which are joined by the arcuate perimeteral edges 25, 26. Each arcuate perimeter edge 25, 26 has a convex curvature which reaches a maximum deviation from the mid-point at approximately the longitudinal center of the pad. As best shown in FIG. 4, the pad has a substantially flat base portion 27 and a working surface 29 termed the template surface herein. The template surface 29 has a central depressed region 30 conforming to the spinal portion of the user's back. Flanking both sides of central hollow region 30, which extends from the top to the bottom edges 25, 26, are a pair of plateau regions 32, 33 arranged to contact the erector spinae muscles of the wearer's back. Each plateau region tapers downwardly in the outward direction to an essentially flat region 34, 35. Each of the flat regions 34, 35 then blends into the respective edge 23, 22. A plurality of ventilation holes 38 are formed through the pad 20.

The pad 20 is made from any suitable stiff but resilient material which will provide a non-conforming contour to the wearer's lower back region under normal use and in the absence of excessive forces. The preferred material for pad 20 is ethylene vinyl acetate having the following characteristics:

| hardness | 38° ± 3 |
| density | 0.26 gm/cc. |
| tensile strength | 7 |
| elongation | 400% |
| blowing | 11 |

The pad has an ovalized center region having a maximum length of around eight inches and a minimum width of about four inches. The plateau regions 32, 33 are spaced from the central hollow 30 by approximately one and a half inches and have a maximum thickness of about one and one-eighth inch. The thickness in the hollow region 30 is about three-quarter inch, and this hollow bridges the protruding spinal processes of the wearer. The raised surface areas 32, 33 approximate the average lordotic curve of a wearer, which greatly assists in maintaining proper posture.

In use, the pad 20 is installed within the belt 10, and the belt is arranged about the waist of the user as suggested in FIG. 2. When in place, the pad 20 rests at an angle 21, which may be about 7°, with the template surface 29 of the orthopedic pad 20 resting against the wearer's back in the lower back region. The plateau regions 32, 33 make surface contact with the erector spinae muscles of the wearer through the skin, and the central hollow region 30 accommodates the bony protrusions of the spine. The pad responds to extension of the back away from the idealized posture represented by the template surface by opposing such extension due to the relative stiffness of the material. Flexion is opposed by the natural tendency of the proprioceptors of the back to adapt to and follow a smooth surface.

It should be noted that, during muscle relaxation, the pad 20 moves away from the spine as an integral unit which allows the muscle and ligament structure of the back to provide its own support. This tends to substantially reduce or eliminate atrophy of the back muscles.

Figure 5:
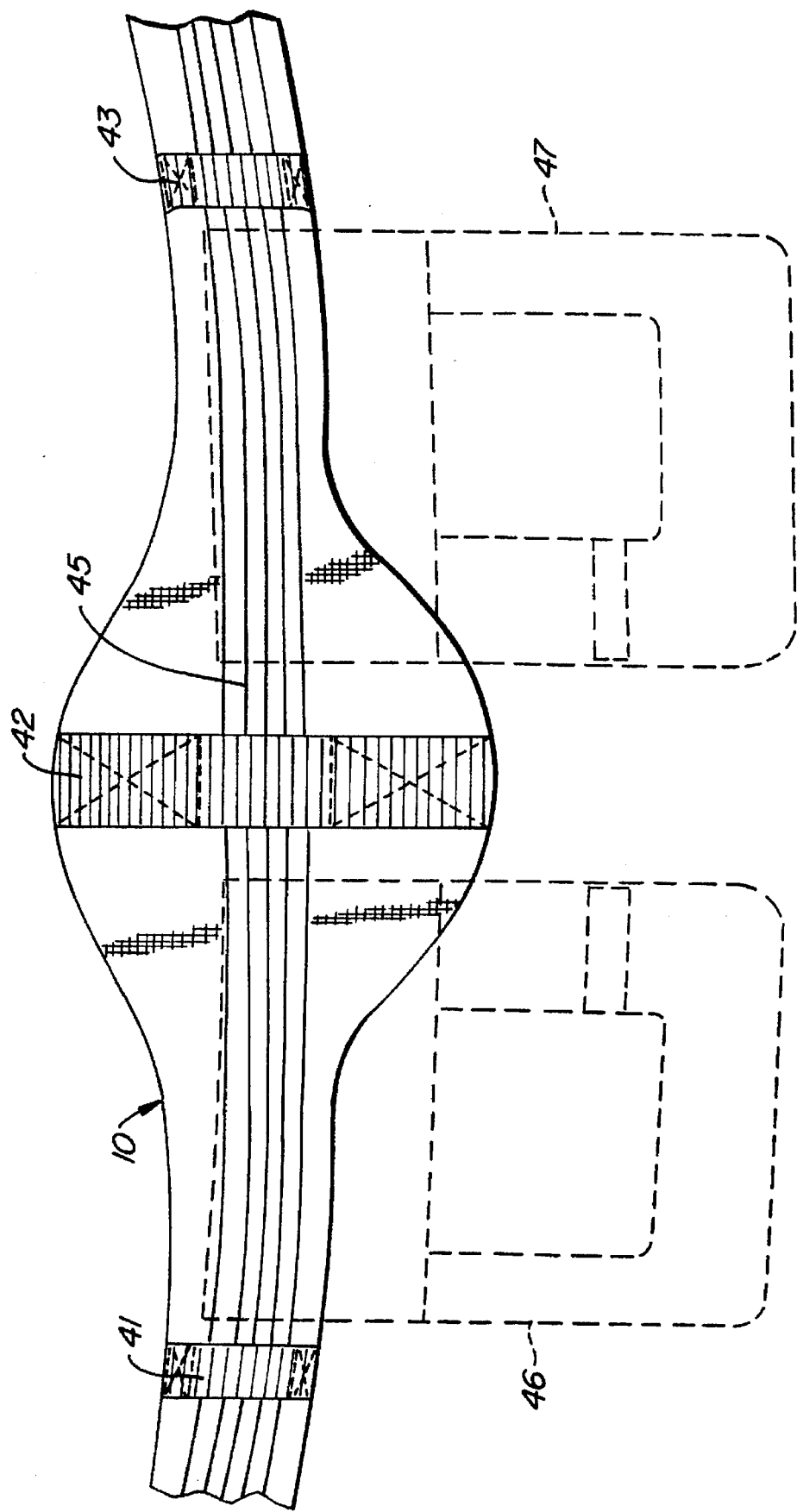
FIG. 5 is a plan view partially broken away of an alternate embodiment of the invention suitable for use with various tool carriers.

FIG. 5 illustrates an alternate embodiment of the invention which is especially suitable for use as a workman's orthopedic device. As seen in this Fig., the belt is provided with a plurality (three illustrated) of secondary belt loops 41, 42 and 43. These loops are attached to the main belt 10 in any suitable fashion, such as by stitching at appropriate intervals, and provide guideloops for a secondary belt 45. Secondary belt 45 serves as a belt support for tool holsters such as the holsters 46, 47 illustrated in broken lines. The holsters 46, 47 may be of any suitable design for carrying the tools of interest to a particular workman, such as pliers, screwdrivers, wire cutters, hammers, etc. The holsters are attached by threading the secondary belt 45 through the holster flaps. The belt 10 shown in FIG. 5 uses the same orthopedic pad 20 as that described above.

As will now be apparent, the invention provides an effective orthopedic support for the lower back region of a wearer. The device is convenient in use and inexpensive to manufacture. The pad is arranged at the proper angle when the belt is installed so as to approximate the average lordotic curve of a user.

While the above provides a full and complete disclosure of the preferred embodiment of the invention, various modifications, alternate constructions and equivalents will occur to those skilled in the art. For example, although specific materials have been described with reference to the belt, the closure and the pad, other equivalent materials may be employed, as desired. Therefore, the above descriptions and illustrations should not be construed as limiting the scope of the invention which is defined by the appended claims.

What is claimed is:

1. For use with a lumbosacral support system, a unitary orthopedic pad having an upper margin and a lower margin, said pad having a smoothly contoured template surface bounded by said margins with a central trough portion extending between said upper and lower margins for accommodating the spinal processes of a wearer when the pad is pressed against the lumbar region, and a pair of raised plateau regions flanking said central trough portion for contacting the erector spinae muscles of the wearer to provide support therefor, the template surface of said pad having a smoothly curving, physiologically nonconforming surface contour through the central region thereof approximating the lordotic curve of a wearer, to assist maintaining proper spinal posture.

2. The invention of claim 1 wherein said pad is fabricated from a compressed foam material.

3. The invention of claim 1 wherein said pad is fabricated from ethylene vinyl acetate.

4. An orthopedic pad, for use with a lumbosacral support system, comprising:

a body having upper and lower edges;

the body having a template surface, adapted to press against the lumbosacral region of the user, having a vertically oriented central trough region and a pair of raised plateau regions flanking the central trough region for contacting the erector spinae muscles of the user; and the raised plateau regions of the template surface having a smoothly curving, physiologically nonconforming surface contour approximating the lordotic curve of the user so to assist maintaining proper spinal posture.

5. The pad of claim 4 wherein the body is a one-piece stiff foam body.

6. An orthopedic pad, for use with a lumbosacral support system, comprising:

a one-piece stiff foam body having upper and lower edges;

the body having a template surface, adapted to press against the lumbosacral region of the user, having a vertically oriented central trough region and a pair of raised plateau regions flanking the central trough region for contracting the erector spinae muscles of the user; and the raised plateau regions of the template surface having a smoothly curving, physiologically nonconforming surface contour approximating the lordotic curve of the user so to assist maintaining proper spinal posture, the raised plateau regions of the template surface having a hardness of about 35° to about 41°.

7. For use with a lumbosacral support system, a unitary orthopedic pad having an upper margin and a lower margin, said pad having a smoothly contoured template surface bounded by said margins with a central trough portion extending between said upper and lower margins for accommodating the spinal processes of a wearer when the pad is pressed against the lumbar region, and a pair of raised plateau regions flanking said central trough portion for contacting the erector spinae muscles of the wearer to provide support therefor, the template surface of said pad having a smoothly curving, physiologically nonconforming surface contour through the central region thereof approximating the lordotic curve of a wearer, to assist maintaining proper spinal posture, wherein said template surface has a hardness of between about 35 and about 41 degrees.

8. For use with a lumbosacral support system, a unitary orthopedic pad having an upper margin and a lower margin, said pad having a smoothly contoured template surface bounded by said margins with a central trough portion extending between said upper and lower margins for accommodating the spinal processes of a wearer when the pad is pressed against the lumbar region, and a pair of raised plateau regions flanking said central trough portion for contacting the erector spinae muscles of the wearer to provide support therefor, the template surface of said pad having a smoothly curving, physiologically nonconforming surface contour through the central region thereof approximating the lordotic curve of a wearer, to assist maintaining proper spinal posture, wherein said pad has a maximum width in the area of the central trough portion of substantially nine inches and top and said bottom edges have a convex curvature.

9. The invention of claim 8 wherein said pad has a thickness in the raised plateau regions of approximately one and one eighth inches.

10. the invention of claim 8 wherein the maximum thickness of said pad in the central trough portion is approximately three-quarter inch.

11. An orthopedic pad, for use with a lumbosacral support system, comprising:

a body having upper and lower edges;

the body having a template surface, adapted to press against the lumbosacral region of the user, having a vertically oriented central trough region and a pair of raised plateau regions flanking the central trough region for contacting the erector spinae muscles of the user; and the raised plateau regions of the template surface have a smoothly curving, physiologically nonconforming surface contour approximating the lordotic curve of the user os to assist maintaining proper spinal posture, the raised plateau regions of the template surface being of a stiff foam material having a hardness of about 35 to 41 degrees.

* * * * *